(12) United States Patent
Cazzini

(10) Patent No.: US 9,050,412 B2
(45) Date of Patent: Jun. 9, 2015

(54) METHOD FOR MONITORING AND CONTROLLING PERITONEAL DIALYSIS

(71) Applicants: Baxter International Inc., Deerfield, IL (US); Baxter Healthcare S.A., Glattpark (Opfikon) (CH)

(72) Inventor: Karl H. Cazzini, Lindenhurst, IL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 388 days.

(21) Appl. No.: 13/682,423

(22) Filed: Nov. 20, 2012

(65) Prior Publication Data

US 2013/0079705 A1  Mar. 28, 2013

Related U.S. Application Data

(63) Continuation of application No. 12/696,831, filed on Jan. 29, 2010, now Pat. No. 8,337,448.

(51) Int. Cl.
*A61M 1/28* (2006.01)
*G08B 21/24* (2006.01)
*H01H 35/42* (2006.01)

(52) U.S. Cl.
CPC ........... *A61M 1/28* (2013.01); *A61M 2205/581* (2013.01); *A61M 2205/583* (2013.01); *H01H 35/42* (2013.01); *G08B 21/24* (2013.01)

(58) Field of Classification Search
CPC ......... A61M 1/28; A61M 1/282; A61M 1/30; A61M 1/307; A61M 1/284; A61M 2205/581; A61M 2205/583; G08B 21/24; H01H 35/42

USPC ........................................................ 604/29
See application file for complete search history.

(56) References Cited

U.S. PATENT DOCUMENTS

| | | | |
|---|---|---|---|
| 4,193,068 A | 3/1980 | Ziccardi | |
| 2006/0241543 A1* | 10/2006 | Gura | 604/5.01 |
| 2008/0217245 A1 | 9/2008 | Rambod et al. | |
| 2009/0099419 A1* | 4/2009 | Matsumoto | 600/118 |
| 2009/0275881 A1* | 11/2009 | Lo et al. | 604/28 |

FOREIGN PATENT DOCUMENTS

DE  10 2009 004 018   2/2014

OTHER PUBLICATIONS

International Search Report and Written Opinion for International Application No. PCT/US2011/021821 mailed on May 9, 2011.
International Search Report and Written Opinion for International Application No. PCT/US2011/021821 mailed on Oct. 4, 2011.

* cited by examiner

*Primary Examiner* — Theodore Stigell
(74) *Attorney, Agent, or Firm* — K&L Gates LLP (57) ABSTRACT

A dialysis apparatus includes a housing; a first electrical contact carried by the housing; a hydrogel material located within the housing; a second electrical contact connected to the hydrogel material, the hydrogel material located so as to be contacted by a liquid flowing through the housing; and wherein the hydrogel material expands as the material absorbs the liquid such that the second electrical contact is moved and eventually engage the first electrical contact.

20 Claims, 5 Drawing Sheets

METHOD FOR MONITORING AND CONTROLLING PERITONEAL DIALYSIS

PRIORITY CLAIM

This application claims priority to and the benefit as a continuation application of U.S. patent application Ser. No. 12/696,831, filed Jan. 29, 2010, now U.S. Pat. No. 8,337,448, issued Dec. 25, 2012, the entire contents of which are incorporated herein by reference and relied upon.

BACKGROUND

The present disclosure relates to medical fluid delivery and in particular to peritoneal dialysis fluid delivery.

Due to disease or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

One type of dialysis is peritoneal dialysis. Peritoneal dialysis uses a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD") and automated peritoneal dialysis ("APD"). CAPD is a manual dialysis treatment, in which the patient connects an implanted catheter to a drain and allows a spent dialysate fluid to drain from the patient's peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. APD is similar to CAPD in that the dialysis treatment includes a drain, fill, and dwell cycle. APD machines, however, perform three to four cycles of peritoneal dialysis treatment automatically, typically overnight while the patient sleeps. Like CAPD, APD machines connect fluidly to an implanted catheter, to one or more sources or bags of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure. As with the manual process, several drain, fill, and dwell cycles will occur during APD. A "last fill" is typically used at the end of APD, which remains in the peritoneal cavity of the patient when the patient disconnects from the dialysis machine for the day.

For both APD and CAPD it is desirable to optimize dwell time such that the dialysis solution remains inside the patient for as long as the fluid is efficiently absorbing waste or ultrafiltration ("UF"). When the discharge fluid becomes "spent", that is, it is not efficiently absorbing waste or UF, the dwell should be ended and a drain of the spent fluid should begin. It is desirable, especially for CAPD, to have a way to control the dwell time to be the optimized time and to notify the patient the dwell time has expired. In the case of APD, such information is also useful especially when the patient has disconnected himself or herself from the APD machine.

SUMMARY

The present disclosure sets forth an apparatus and method for determining, indicating and controlling an end of a patient dwell period for peritoneal dialysis ("PD"). The apparatus and method may be used to control an APD machine and is especially useful with CAPD. In general, a material is used, such as a hydrogel material, which increases in volume in a controlled and predictable way as the material absorbs water or dialysis fluid over time. The polymer material or hydrogel absorbs the liquid causing the material to expand predictability. The exterior of the material is fitted with an electrical contact or contacts. As the material expands, the contact moves outwardly. Eventually the contact is moved enough, such that it contacts a stationary contact. The material is specifically configured such that the duration of the expansion up until the contacts mate coincides with the patient's optimal dwell time.

Once the contacts are mated, a circuit is completed and a signal is delivered to an APD machine, which can signal a switch from a dwell phase to a drain phase. Alternatively, the contact closure sounds an alarm or alert to a patient performing CAPD. The alert tells the CAPD patient to end a dwell phase and begin draining. The apparatus therefore acts as a timer to time out an optimal dwell, without the need for a power source for its movement.

The hydrogel material needs to be in contact with fluid over the course of treatment. It is contemplated to place the hydrogel apparatus in the patient line or in combination with the patient's transfer set, so that fresh fluid remains in contact with the material during the entire dwell. In an APD application, the apparatus may be incorporated with a disposable cassette assuming that at least the apparatus associated portion of the cassette remains primed during the entire dwell.

The timing of the apparatus is controlled via a number of parameters, such as, material type, porosity or percent open, and size. For example, a certain polymer hydrogel material may swell more quickly than other polymer hydrogels. A hydrogel that is more open than another hydrogel may swell more quickly. A hydrogel material that is larger than another hydrogel material may swell more slowly because it requires more water to become saturated.

In an alternative embodiment, the electrical contact is not a physical contact. For example, the hydrogel material could be configured to change a capacitance ("ΔC") between two parallel (or concentric) plates to form a parallel plate capacitor. As the hydrogel material hydrates, the distance between capacitor plates decreases and the resulting capacitance increases.

It is accordingly an advantage of the present disclosure to provide a device and method for optimizing a dwell period for peritoneal dialysis.

It is another advantage of the present disclosure to provide a device and method that times out or alarms or alerts when a patient's dwell period has ended.

It is a further advantage of the present disclosure to provide a dwell period timer or alerting apparatus that does not require external power for its movement.

It is still another advantage of the present disclosure to provide dwell period timer or alerting apparatus that can be incorporated readily into a CAPD or APD disposable and sterilized via a preferred method.

Additional features and advantages are described herein, and will be apparent from the following Detailed Description and the figures.

DETAILED DESCRIPTION

Referring now to the drawings and in particular to FIGS. 1 to 4, the volume increasing material control apparatus of the present disclosure, denoted generally as apparatus 10, may be placed in a number of places in an automated peritoneal dialysis ("APD") disposable or continuous ambulatory peritoneal dialysis ("CAPD") disposable set. It is accordingly contemplated to use apparatus 10 in connection with APD and CAPD. It should be appreciated however, that apparatus 10 is not limited to peritoneal dialysis and may have application in hemodialysis or other renal blood treating system. Further alternatively, apparatus 10 may be used with other medical fluid systems and applications.

Figure 1:
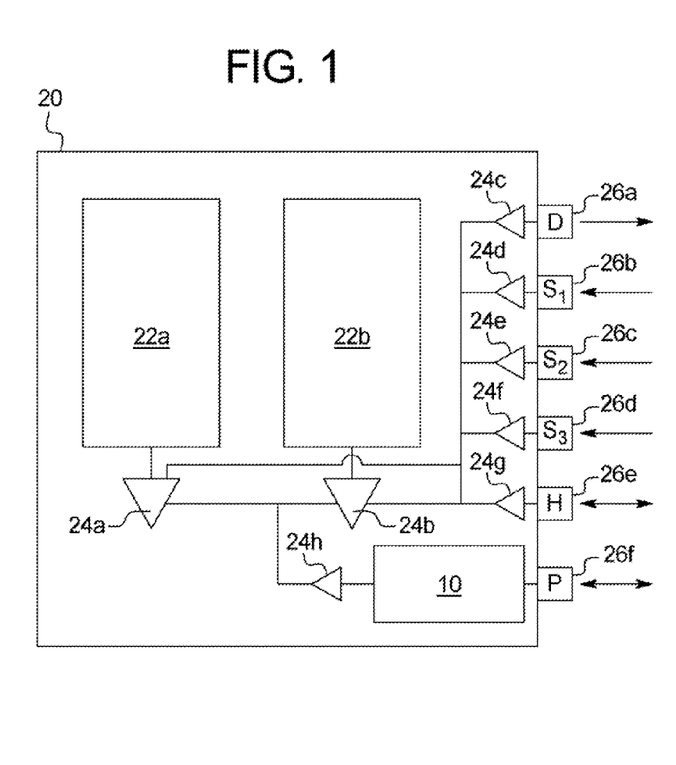
FIG. 1 is a schematic diagram of a disposable pumping and valve cassette, which houses a volume increasing material control switch or timer of the present disclosure.

FIG. 1 illustrates apparatus 10 incorporated into a disposable pumping and valving cassette 20. Pumping and valving cassettes are known in the art. One suitable cassette for integration with volume increasing material apparatus 10 is disclosed in U.S. Pat. No. 5,350,357, the pertinent contents of which incorporated herein by reference. Generally, cassette 20 includes a pair of pumping chambers 22a and 22b that communicate fluidly with a plurality of valve chambers 24a to 24h, which separate pump chambers 22a and 22b from a plurality of ports 26a to 26d and from apparatus 10. Port 26a is a drain port to which a drain line carries spent dialysate from cassette 20 to a house drain or drain container. Ports 26b to 26d are supply ports that connect to supply lines that lead to different supplies of dialysis fluid or dialysate. Port 26e is a heater port that connects to a heater line that extends to a heater bag. Pumps 22a and 22b pump fluid to the heater, which heats dialysate, after which the pumps pull heated fluid from the heater bag and push the heated fluid towards patient port 26f through apparatus 10.

Pumps 22a and 22b fill the patient through apparatus 10, port 26f and a patient line, which extends to a patient's peritoneum (or typically to a transfer set connected to the patient). Once the patient is filled with fluid, valve chamber 24h is closed, such that apparatus 10 remains filled with fluid. Apparatus 10 includes a volume increasing material, such as a hydrogel discussed in detail below, which becomes swollen or swells over time as fluid remains within apparatus 10.

Figure 2:
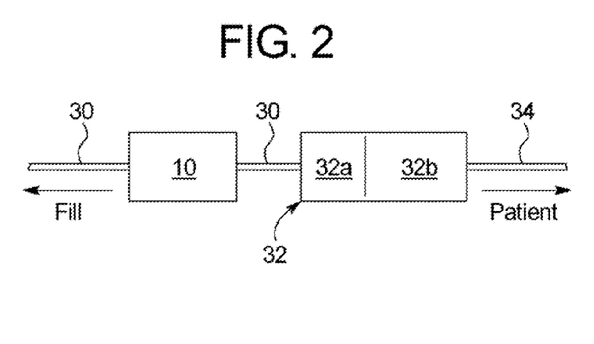
FIG. 2 is a schematic illustration of a patient line showing a patient transfer set and an embodiment of a volume increasing material control switch or timer of the present disclosure.
Figure 3:
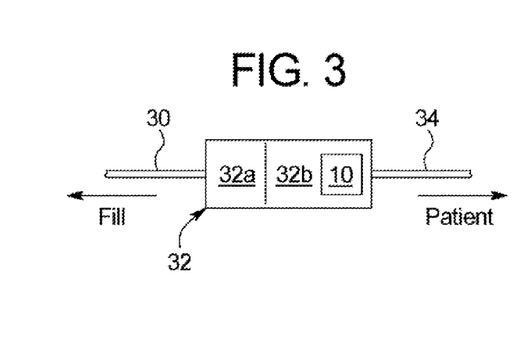
FIG. 3 illustrates a patient's supply line having a patient transfer set that incorporates an embodiment of the volume increasing material control switch or timer of the present disclosure.
Figure 4:
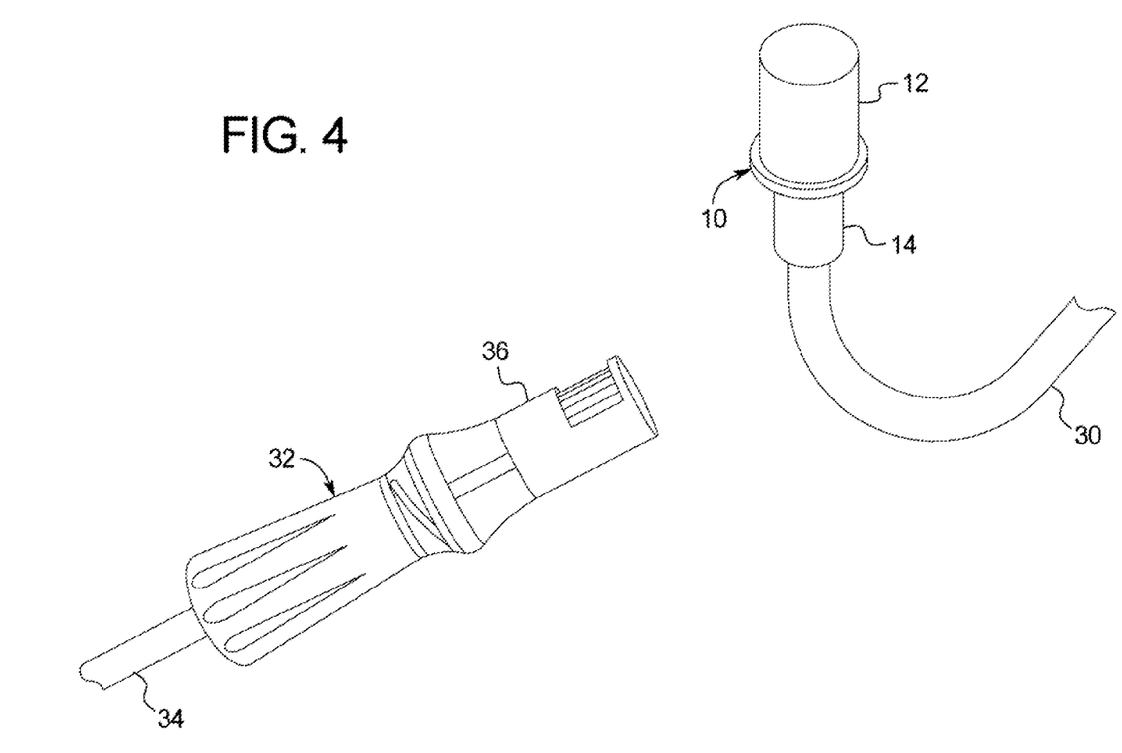
FIG. 4 is a perspective view of one embodiment of the present disclosure in which the volume increasing material control switch is incorporated into a cap on the end of a supply line, wherein the cap is transferred to the patient's transfer set after fill.

FIG. 1 shows an application in which apparatus 10 is used to perform APD. FIGS. 2 through 4 illustrate applications in which apparatus 10 is used with an APD or a CAPD therapy. FIG. 2 illustrates a fill line 30, which runs to either patient port 26f or cassette 20 of FIG. 1 for APD or to a supply bag for CAPD. Fill line 30 connects to a patient transfer set 32, which has a disposable portion 32a located at the end of fill line 30 and a reused patient port 32b, connected to a patient catheter line 34, which extends to an indwelling catheter that extends inside the patient's peritoneal cavity. The patient thus connects disposable portion 32a to patient portion 32b of transfer set 32 to establish fluid communication between cassette 20 or a fresh fluid source and the patient. In FIG. 2, apparatus 10 is placed in fill line 30. The therapy is controlled such that fill line 30 is always full during dwell so that apparatus 10 continues to be filled with dialysate even after the patient's peritoneum is full. Fill line 30 either remains connected to transfer set 32 during dwell or is disconnected from the transfer set while full and clamped. In either case, a volume increasing material placed within apparatus 10 is constantly contacted by fluid. Indeed for both the embodiments of FIGS. 1 and 2, the patient can place a clamp on line 30 near connector 32a or can alternatively cap connector 32a to hold fluid within fill line 30, so that the fluid remains in contact with the volume increasing material placed within apparatus 10.

In FIG. 3, apparatus 10 is incorporated into transfer set 32. FIG. 3 shows apparatus 10 incorporated into the patient portion 32b of transfer set 32, such that apparatus 10 is reused. Alternatively, apparatus 10 is placed within disposable section 32a of transfer set 32, such that apparatus 10 is not reused. In certain PD applications, especially in connection with CAPD, which may be performed during the day, the patient disconnects disposable transfer set portion 32a from patent transfer set portion 32b. Transfer set portion 34b includes an integrated twist clamp that the patient can close before disconnection. Such twist clamp seals the fluid so that it remains in contact with apparatus 10 in the embodiment of FIG. 3.

FIG. 4 illustrates one preferred embodiment of the present disclosure. Here, apparatus 10 is fitted at the end of fill line 30 with a cap 12. Apparatus is mated removeably and resealably with a connector 14, which is fixed in sealed engagement with fill line 30. For example, connector 14 can have a male luer tip (not illustrated) that is inserted through a resealable septum located at the proximal (or fill line 30) end of apparatus 10. When connector 14 and fill line 30 are removed from apparatus 10, the septum reseals the end of apparatus 10.

In FIG. 4, transfer set 32 is fitted with a removable cap 36. The distal end of apparatus 10 is configured to removeably and sealingly mate with the connecting end (not seen in FIG. 4) of transfer set 40, e.g., via a threaded or sealed luer connection. When caps 12 and 32 are removed from apparatus 10 and transfer set 32, the user or patient releasably and sealingly connects apparatus 10 to transfer set 32. Thereafter, the patient is filled via a supply of dialysis fluid, through fill line 30, through connector 14, through apparatus 10, through transfer set 32, through patient line 14, and into the patient. The fill volume is enough to maintain fluid contact with apparatus 10 at all times during and after patient filling, so as to provide an accurate indicator of how long the fluid has been delivered to the patient. Once the fill is completed, connector 14 is removed from apparatus 10, at which time apparatus 10 reseals itself.

When apparatus 10 indicates that the dwell time for the previous fill has elapsed, the patient can either connect/insert a drain line to/into apparatus 10 or remove apparatus 10 and connect the drain line directly to transfer set 32. Eventually, apparatus is removed from transfer set 32 and is discarded. The next fill will be supplied using a new supply container, new fill line 30 and a new apparatus 10 with cap 12 and connector 14.

Figure 5A:
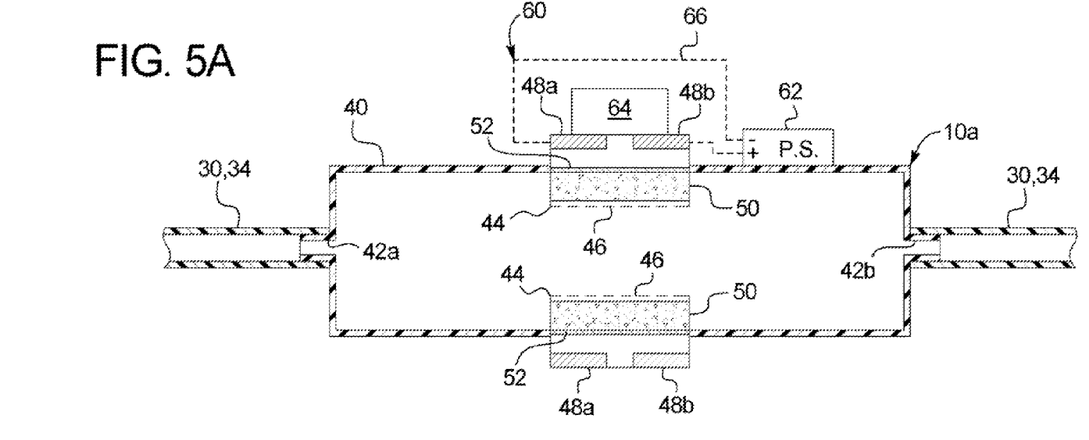
FIGS. 5A and 5B are schematic sectioned views illustrating one embodiment of a volume increasing material control switch or timer of the present disclosure in unactivated and activated conditions, respectively.
Figure 5B:
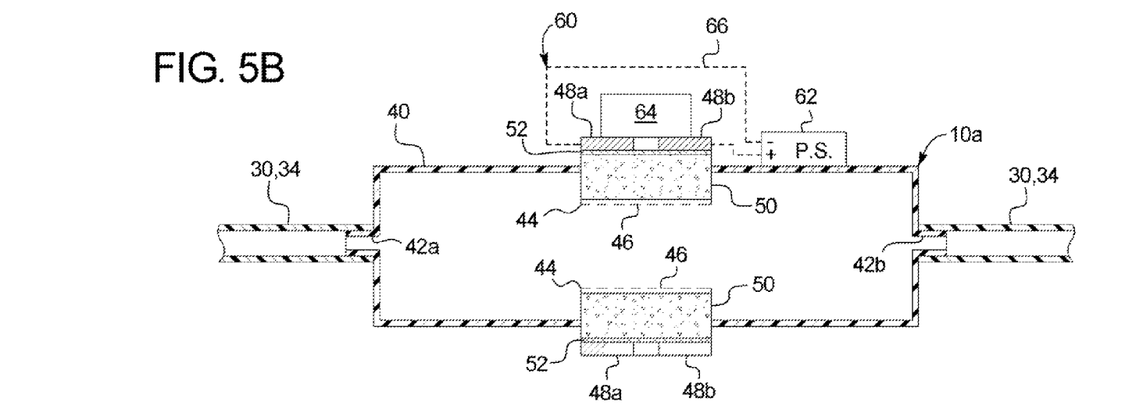

Referring now to FIGS. 5A and 5B, apparatus 10a illustrates one embodiment for apparatus 10 shown generally in FIGS. 1 to 4. Apparatus 10a includes a housing 40 having an input port 42a and an output port 42b. For purposes of illustration, ports 42a and 42b are shown connected fluidly to fill line 30 or patient catheter line 34, in connection with the application embodiments of FIGS. 2 and 4, respectively. It should be appreciated however that apparatus 10a can operate alternatively with cassette 20 of FIG. 1 or with transfer set 32 as shown in FIG. 3. In either case, apparatus 10a may or may not require ports, such as ports 42a and 42b. Housing 40 is made of a suitable medical grade plastic, such as medical grade polyvinyl-chloride ("PVC") or a medical grade non-PVC plastic, such as silicone.

Housing 40 also carries or forms a chamber 44 that houses a volume increasing material 50, such as a hydrogel. Either one or both of chamber 44 and hydrogel material 50 may have a collar shape that encircles a central axis through housing 40.

Hydrogel material 50 is in general a network of polymer chains that are water insoluble. Hydrogel material 50 is a highly absorbent, natural or synthetic polymer that may absorb over ninety-nine percent water. Hydrogels are also typically flexible and can be formed into a desired shape. One suitable material for hydrogel 50 is described in U.S. Pat. No. 6,878,384, entitled, "Hydrogels That Undergo Volumetric Expansion In Response To Changes In Their Environment And Their Methods Of Manufacture And Use", assigned to MicroVention, Inc. (Aliso Viego, Calif.), the entire contents of which are incorporated herein by reference and relied upon.

Chamber 44 includes a water permeable membrane or mesh 46 that allows liquid, such as dialysis fluid, to permeate through surface 46 and contact hydrogel material 50. In an embodiment, hydrogel material 50 seals to permeable surface 46, such that water cannot fill within chamber 44 to create fluid communication between a pair of contacts 48a and 48b located along an outer surface of chamber 44. A contact 52 is likewise placed along an outer surface of volume increasing or hydrogel material 50. FIG. 5A shows an initial position, for example at the beginning of a patient dwell, in which contact 52 on material 50 does not contact create electrical continuity between contact 48a and 48b. In FIG. 5B, for example at the end of a desired patient dwell, material 50 has swollen or increased in volume, such that contact 52 now makes physical contact with contacts 48a and 48b, thus completing an electrical circuit 60 provided by apparatus 10a.

Electrical circuit 60 includes a power supply 62, that powers an output device 64 via an electrical line 66. In an embodiment, power supply 62 is a DC battery supply, such as a rechargeable battery. Electrical line 66 can be actual wire or a trace provided on a printed circuit board. Output device 64 can be a sonic and/or optical output device that for example alerts a CAPD patient when an optimal dwell time has been completed, which coincides with the mating of contact 54 with contacts 48a and 48b. In a CAPD example, the flashing light or audible sound at output device 64 causes the patient to begin the patient drain manually.

Output device 64 is alternatively a wireless transmitter or transceiver that sends a wireless signal to a receiver or transceiver located on or at the APD machine. Here, apparatus 10a sends a signal to the APD machine informing the machine that the optimal dwell has ended, which again coincides with the mating of contact 52 with contacts 48a and 48b. The signal sent from transmitter or transceiver 64 is processed at the APD machine, which in turn causes a patient to drain to begin, for example. In a further alternative embodiment, electrical line 66 of circuit 60 may extend to the APD device, such that the contact closure can be sensed at the APD machine, upon which appropriate action is taken.

As discussed above, each patient has different physiological characteristics and responds to therapy in the patient's own way. Patients are typically categorized into four different transport modes, such as high, high-average, low and low-average. These transport modes in combination with therapy parameters, such as type of solution used, volume of solution used and other factors affects the overall dialysis performance. U.S. patent application Ser. No. 12/431,458, entitled "Optimizing Therapy Outcomes For Peritoneal Dialysis", filed Apr. 27, 2009, assigned to the assignee of the present disclosure, the entire contents of which are incorporated herein by reference sets forth an apparatus and method for determining the patient's optimal dwell time for a given set of therapy parameters and based on the patient's physical characteristics and response to treatment.

Once that optimal dwell time is known, it is contemplated to structure expanding volume material 50, such that it expands at a rate so that contact 52 engages contacts 48a and 48b at or near the optimal dwell time ending duration. It is contemplated to vary the type of polymer used for material 50. It is further contemplated to vary the amount of openness or porosity of material 50.

Still further, it is contemplated to vary the size or thickness for material 50 based on the optimal dwell time. For example, in FIG. 5A a narrower hydrogel 50 will have more space to consume and thus may be used to indicate a longer dwell period. Alternatively, an inner diameter of material 50 (assuming it is collar shaped) can be reduced, such that the wall thickness of the collar increased for a given outside diameter of the collar. This could increase the amount of material that needs to be saturated for expansion, which would also slow the expansion process and be used for a longer dwell duration.

The above variables are tested experimentally to derive a combination that yields a particular dwell time. The patient's optimal dwell time is then matched with a like dwell time of a particular combination of variables for material 50.

While apparatus 10a is shown with material 50 having an electrical contact 52, it is contemplated that a highly fluid absorbed material 50 may be conductive enough to create a repeatable and sensitive electrical continuity between contact 48a and 48b, such that material contact 52 is not needed or used. For example, hydrogel material 50 itself may form an electrode comprised of a polyethylene oxide or polyvinyl pyrrolidone.

Figure 6A:
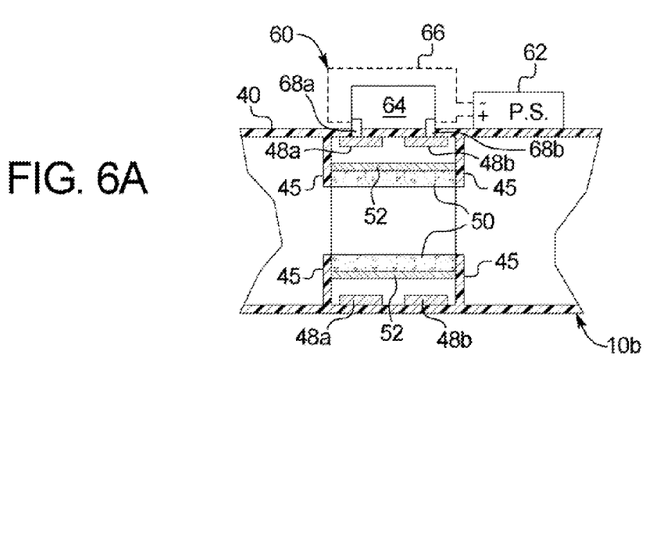
FIGS. 6A and 6B are schematic sectioned views illustrating a second embodiment of a volume increasing material control switch or timer of the present disclosure in unactivated and activated conditions, respectively.
Figure 6B:
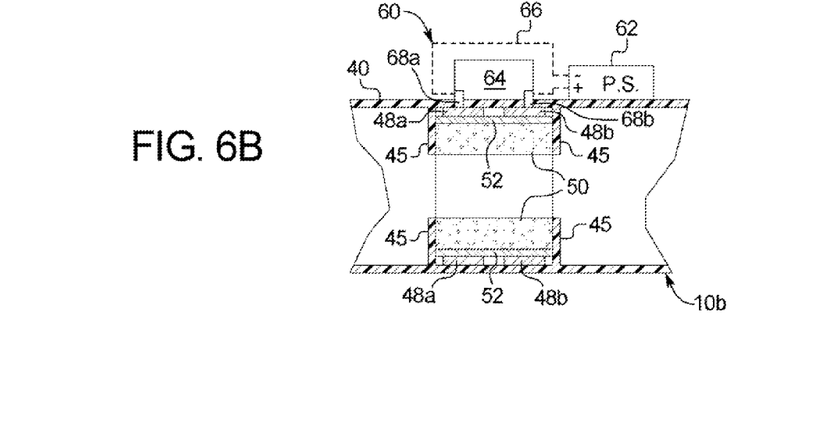

Referring now to FIGS. 6A and 6B, apparatus 10b illustrates another embodiment for apparatus 10 shown generally in FIGS. 1 to 4. Here, housing 40 includes internal sidewall 45 that encases hydrogel material 50 except for its inner surface. In an embodiment, hydrogel material 50 seals to inner surfaces of walls 45, such that dialysis fluid cannot travel around material 50 and engage contact 48a and 48b to falsely create electrical continuity. Contacts 48a and 48b in this alternative embodiment are placed on the inside surface of housing 40. Power supply 62, output device 64, electrical lines 66 of circuit 60 as discussed above (including all alternatives) are used again for apparatus 10b of FIGS. 6A and 6B. An additional set of contacts 68a and 68b is provided that pierce the wall of housing 40 to electrically connect inner electrodes 48a and 48b with output device 64.

FIG. 6B illustrates that apparatus 10b operates in a very similar manner as apparatus 10a. At a desired end of a dwell duration, hydrogel material 50 is configured such that it has expanded, so that electrical continuity begins to exist between contacts 48a and 48b and likewise contacts 68a and 68b. A separate electrode 52 may or may not be placed on an outer surface of hydrogel material 50 as has been discussed herein.

Figure 7:
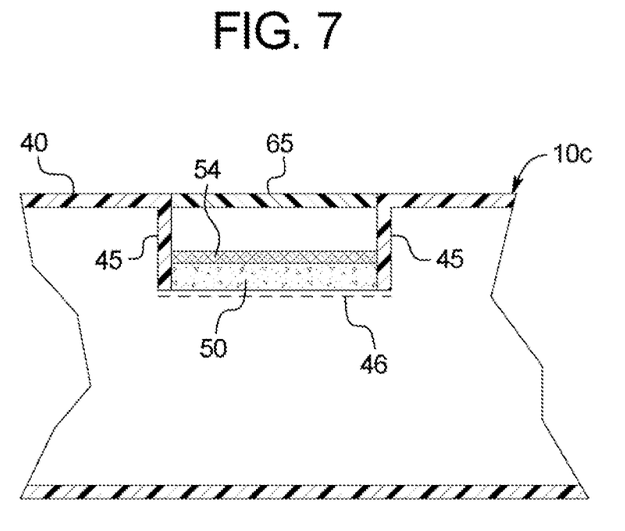
FIG. 7 is a schematic sectioned view of a further alternative embodiment of a volume increasing material control switch or timer of the present disclosure.

Referring now to FIG. 7, apparatus 10c illustrates a further alternative embodiment for apparatus 10 shown in FIGS. 1 to 4. Apparatus 10c includes sidewalls 45, similar to those of FIGS. 6A and 6B, which along with a perforated bottom wall 46 support expanding polymer or hydrogel material 50. Hydrogel material 50 is coated on its outer surface with a colored marker, such as an opaque black, red, green or other suitable color marker. Housing 40 seals a transparent or translucent window 65, such as a plastic or glass window. The size and/or brightness of marker 54 are/is configured such that marker 54 is not viewable (or not as viewable) until it reaches window 65. Apparatus 10c is accordingly a purely mechanical apparatus and does not require a power supply. Apparatus 10c may be better suited for CAPD and/or for a single fill version of apparatus 10, such as that of FIG. 4.

In still another alternative embodiment for apparatus 10 shown generally in FIGS. 1 to 4, a physical electrical contact does not take place. For example, the hydrogel material could be configured to change a capacitance ("ΔC") between two parallel (or concentric) plates to form a parallel plate capacitor. The capacitance is modeled by $C = E * \beta_o * A/d$, where E is the magnitude of the electric field between two parallel plates separated by distance d, $\epsilon_o$ is the permittivity of free space and a constant equal to $8.85 \times 10^{-12}$ F/m, and A is the cross-sectional area of one of the plates. As the hydrogel material hydrates, d decreases and capacitance C increases.

Aspects of the subject matter described herein may be useful alone or in combination one or more other aspect described herein. Without limiting the foregoing description, in a first aspect of the present disclosure, a dialysis apparatus includes: a housing; a first electrical contact carried by the housing; a hydrogel material located within the housing; a second electrical contact connected to the hydrogel material, the hydrogel material located so as to be contacted by a liquid flowing through the housing; and wherein the hydrogel material expands as the material absorbs the liquid such that the second electrical contact is moved and eventually engage the first electrical contact.

In accordance with a second aspect of the present disclosure, which may be used in combination with the first aspect, the engagement of the first and second contacts completes an electrical circuit.

In accordance with a third aspect of the present disclosure, which may be used in combination with the second aspect, the electrical circuit includes an alarm or alerting device that is activated upon the engagement of the first and second contacts.

In accordance with a fourth aspect of the present disclosure, which may be used in combination with the second aspect, the electrical circuit is battery powered.

In accordance with a fifth aspect of the present disclosure, which may be used in combination with any one or more of the preceding aspects, the engagement of the first and second contacts signals an end of a dialysate dwell period.

In accordance with a sixth aspect of the present disclosure, which may be used in combination with any one or more of the preceding aspects, the first electrical contact is located on an inner wall of the housing, while the second electrical contact is located on an outer wall of the hydrogel material.

In accordance with a seventh aspect of the present disclosure, which may be used in combination with any one or more of the preceding aspects, the liquid is a dialysis fluid.

In accordance with an eighth aspect of the present disclosure, which may be used in combination with any one or more of the preceding aspects, the dialysis apparatus is used with (i) an automated peritoneal dialysis ("APD") machine or with (ii) a continuous ambulatory peritoneal dialysis ("CAPD") disposable set.

In accordance with a ninth aspect of the present disclosure, which may be used in combination with any one or more of the preceding aspects, the dialysis apparatus is (i) located in a patient supply line, (ii) incorporated into a disposable cassette, (iii) incorporated into a patient's transfer set, and (iv) located in a section of tubing leading from the patient's transfer set to the patient.

In accordance with a tenth aspect of the present disclosure, which may be used in combination with any one or more of the preceding aspects, the hydrogel material is carried by the housing via a member permeable to the liquid.

In accordance with an eleventh aspect of the present disclosure, which may be used in combination with any one or more of the preceding aspects, the first contact includes a pair of contacts, which are placed in electrical or mechanical communication when the second contact engages the first contact.

In accordance with a twelfth aspect of the present disclosure, which may be used in combination with any one or more of the preceding aspects, a dialysis apparatus includes: a housing; first and second contacts covered by the housing; a material located within the housing; and a third electrical contact connected to the material, the material located so as to be contacted by liquid traveling through the housing, and the material configured to expand as the material absorbs the liquid such that the third contact moves into engagement with the first and second contacts.

In accordance with a thirteenth aspect of the present disclosure, which may be used in combination with any one or more of the preceding aspects and the twelfth aspect, the material is a hydrogel material.

In accordance with a fourteenth aspect of the present disclosure, which may be used in combination with any one or more of the preceding aspects and the twelfth aspect, the material is configured such that the engagement of the third contact with the first and second contacts occurs at approximately an end of an optimal dwell duration for a patient.

In accordance with a fifteenth aspect of the present disclosure, which may be used in combination with any one or more of the preceding aspects and the twelfth aspect, wherein at least one of: (i) a type, (ii) a porosity, and (iii) a size of the material is varied to set a particular time needed for the third contact to move into engagement with the first and second contacts.

In accordance with a sixteenth aspect of the present disclosure, which may be used in combination with any one or more of the preceding aspects, a dialysis method includes: filling a patient with dialysis fluid, such that the dialysis fluid remains in contact with a material; allowing the material to swell with dialysis fluid to a certain extent; and indicating that a patient dwell phase should be ended when the material has swollen to the certain extent.

In accordance with a seventeenth aspect of the present disclosure, which may be used in combination with any one or more of the preceding aspects and the sixteenth aspect, wherein the dialysis method includes choosing the material such that a duration needed for the material to swell to the certain extent coincides with an optimal dwell time for the patient.

In accordance with an eighteenth aspect of the present disclosure, which may be used in combination with any one or more of the preceding aspects and the sixteenth aspect, wherein the dialysis method includes mechanically indicating that the patient dwell phase should be ended.

In accordance with a nineteenth aspect of the present disclosure, which may be used in combination with any one or more of the preceding aspects and the sixteenth aspect, wherein the dialysis method includes electrically, audibly or visually indicating that the patient dwell phase should be ended.

In accordance with a twentieth aspect of the present disclosure, which may be used in combination with any one or more of the preceding aspects and the sixteenth aspect, wherein the dialysis method includes locating the material in an apparatus that is transferred from a supply fill line to a transfer set worn by the patient.

In accordance with a twenty-first aspect of the present disclosure, which may be used in combination with any one or more of the preceding aspects and the sixteenth aspect, wherein the dialysis method includes capacitively determining that the material has swollen to the certain extent.

In accordance with a twenty-second aspect of the present disclosure, any of the structure and functionality illustrated and described in connection with FIG. 1 may be used in combination with any one or more of the preceding aspects.

In accordance with a twenty-third aspect of the present disclosure, any of the structure and functionality illustrated and described in connection with FIG. 2 may be used in combination with any one or more of the preceding aspects.

In accordance with a twenty-fourth aspect of the present disclosure, any of the structure and functionality illustrated and described in connection with FIG. 3 may be used in combination with any one or more of the preceding aspects.

In accordance with a twenty-fifth aspect of the present disclosure, any of the structure and functionality illustrated and described in connection with FIG. 4 may be used in combination with any one or more of the preceding aspects.

In accordance with a twenty-sixth aspect of the present disclosure, any of the structure and functionality illustrated and described in connection with FIGS. 5A and 5B may be used in combination with any one or more of the preceding aspects.

In accordance with a twenty-seventh aspect of the present disclosure, any of the structure and functionality illustrated and described in connection with FIGS. 6A and 6B may be used in combination with any one or more of the preceding aspects.

In accordance with a twenty-eighth aspect of the present disclosure, any of the structure and functionality illustrated and described in connection with FIG. 7 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis method comprising:
    filling a patient with dialysis fluid such that the dialysis fluid contacts a material;
    allowing the material to swell via contact with dialysis fluid to a certain extent; and
    indicating that a dwell phase for the patient should be ended when the material has swelled to the certain extent.

2. The dialysis method of claim 1, wherein the material is selected such that a duration needed to allow the material to swell to the certain extent coincides with an optimal dwell time for the patient.

3. The dialysis method of claim 1, which includes mechanically indicating that the dwell phase for the patient should be ended.

4. The dialysis method of claim 1, which includes electrically, audibly or visually indicating that the dwell phase for the patient should be ended.

5. A peritoneal dialysis method comprising:
    flowing a dialysis fluid through a housing of an apparatus so as to contact a hydrogel material carried by the housing;
    enabling the hydrogel material to absorb the dialysis fluid to cause the hydrogel material to expand; and
    allowing the expanding hydrogel material to engage an electrical contact carried by the apparatus housing so as to complete an electrical circuit and indicate an end of a dwell phase for a patient.

6. The peritoneal dialysis method of claim 5, which includes activating an alert upon engagement of the housing electrical contact with the hydrogel material.

7. The peritoneal dialysis method of claim 5, which includes powering the electrical circuit via a battery.

8. The peritoneal dialysis method of claim 5, wherein completing the electrical circuit includes enabling an electrical contact carried by the hydrogel material to engage the electrical contact of the apparatus housing.

9. The peritoneal dialysis method of claim 8, wherein the electrical contact of the apparatus housing is located on an inner wall of the apparatus housing, and the electrical contact of the hydrogel material is located on an outer wall of the hydrogel material.

10. The peritoneal dialysis method of claim 5, which includes operating the apparatus with a dialysis machine or a disposable dialysis set.

11. The peritoneal dialysis method of claim 5, which includes locating the apparatus in (i) a patient supply line, (ii) a disposable cassette; (iii) a patient transfer set, or (iv) a section of tubing leading from a patient transfer set to the patient.

12. The peritoneal dialysis method of claim 5, wherein the electrical contact of the apparatus housing includes two electrical contacts.

13. A peritoneal dialysis method comprising:
allowing a dialysis fluid to flow to a patient;
allowing the dialysis fluid to contact and expand a hydrogel material during a dialysis dwell phase of the patient; and
generating a signal indicative of an end of the dialysis dwell phase for the patient when the expanding hydrogel material completes an electrical circuit.

14. The peritoneal dialysis method of claim 13, which includes generating a visible or audio alert in response to the signal indicative of an end of the dialysis dwell phase for the patient.

15. The peritoneal dialysis method of claim 13, which includes switching from the dialysis dwell phase for the patient to a drain phase for the patient in response to the generated signal.

16. The peritoneal dialysis method of claim 13, which includes allowing the dialysis fluid to remain in contact with the hydrogel material during the entire dialysis dwell phase for the patient.

17. The peritoneal dialysis method of claim 13, which includes controlling the rate at which the hydrogel material expands by selecting the hyrdrogel material based upon at least one of (i) size, (ii) porosity, or (iii) a type of the material.

18. The peritoneal dialysis method of claim 13, wherein the hydrogel material is located in a disposable cassette.

19. The peritoneal dialysis method of claim 13, which includes sending the generated signal wirelessly to an automated peritoneal dialysis machine.

20. The peritoneal dialysis method of claim 13, wherein completing the electrical circuit includes making an electrical contact closure, and which includes disallowing the dialysis fluid from engaging the electrical contact closure.

* * * * *